United States Patent [19]

Collington et al.

[11] Patent Number: 4,851,523
[45] Date of Patent: Jul. 25, 1989

[54] CYCLOPENTYL ETHERS AND THEIR PREPARATION AND PHARMACEUTICAL FORMULATION

[75] Inventors: Eric W. Collington, Knebworth; Harry Finch, Letchworth, both of England

[73] Assignee: Glaxo Group Limited, London, England

[21] Appl. No.: 110,776

[22] Filed: Oct. 21, 1987

[30] Foreign Application Priority Data

Oct. 22, 1986 [GB] United Kingdom ............. 8625321

[51] Int. Cl.⁴ ............... A61K 31/55; A61K 31/557; C07D 323/00
[52] U.S. Cl. ............................ 536/103; 514/925; 560/53; 560/121; 536/46
[58] Field of Search ............ 536/103, 46; 514/212, 514/613, 708, 925, 58; 560/53, 121

[56] References Cited

U.S. PATENT DOCUMENTS 3,857,831 12/1974 Hayashi et al. ............... 536/103
3,979,440 9/1976 Morozowich ................. 514/899
4,178,457 12/1979 Van Horn et al. ............. 560/53
4,304,926 12/1981 Morozowich .................. 560/121

FOREIGN PATENT DOCUMENTS 2174702 11/1986 United Kingdom .

Primary Examiner—Ronald W. Griffin
Attorney, Agent, or Firm—Bernard, Rothwell & Brown

[57] ABSTRACT

Compounds of the general formula (1)

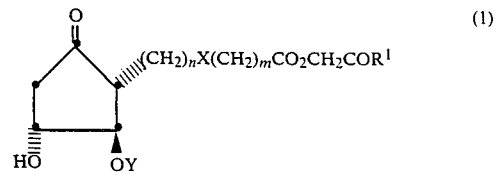

in which
n is 1 or 2;
m is 2–5 and X is —CH=CH— or —CH$_2$—CH$_2$—; or
m is 1–4 and X is —CH=C=CH—;
R$^1$ is phenyl, substituted phenyl or naphthyl;
Y is substituted or unsubstituted 3-phenoxy-2-hydroxypropyl.

These compounds inhibit gastric acid secretion and provide gastrointestinal cytoprotection, and may be formulated for use in the treatment of ulcers.

11 Claims, No Drawings

CYCLOPENTYL ETHERS AND THEIR PREPARATION AND PHARMACEUTICAL FORMULATION

Prostaglandin E$_2$ is a naturally occurring substance which has many physiological actions. For example, it inhibits gastric acid secretion and provides gastrointestinal cytoprotection, lowers blood pressure, stimulates and relaxes smooth muscle, inhibits platelet aggregation and inhibits lipolysis.

Synthetic PGE$_2$ analogues offer the possibility of different potency, longer duration of activity and increased selectivity of action and are therefore of considerable interest.

We have now found a new group of cyclopentyl ethers that have PGE$_2$-type activity. Compounds in this class have a particularly useful profile of biological action. In particular they have shown high potency and improved selectivity as regards the inhibition of gastric acid secretion and gastrointestinal cytoprotection and are therefore of interest in the treatment of ulcers. Compounds according to the invention also have a lipid lowering action and are of interest in the treatment of clinical conditions in which the underlying aetiology is associated with lipid imbalance or hyperlipidemia.

The invention thus provides compounds of the general formula (1)

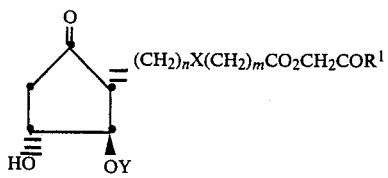

wherein n is 1 or 2;

m is 2–5 and X is cis or trans —CH=CH— or —CH$_2$—CH$_2$—; or m is 1–4 and X is —CH=C=CH—;

R$^1$ is phenyl [optionally substituted by C$_{1-4}$ alkyl, C$_{1-4}$ alkoxy, C$_{1-4}$ alkanoyl, methylthio, metyhlsulphinyl, methylsulphonyl, halogen, —CO$_2$R$^2$ (where R$^2$ is a hydrogen atom or C$_{1-4}$ alkyl or phenyl), —CONR$^3$R$^4$ (where R$^3$ and R$^4$ may be the same or different and are each a hydrogen atom or a C$_{1-4}$ alkyl group), —NHCOR$^2$ (where R$^2$ is as defined above or is a phenyl group optionally substituted by hydroxyl, CH$_3$CONH— or

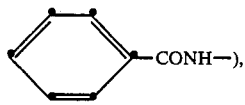

or —NHCONH$_2$, —CH$_2$CH(CONH$_2$)NHCOCH$_3$ or

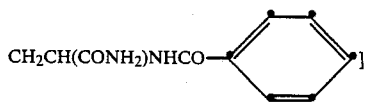

or R$^1$ is 2-naphthyl;

Y is

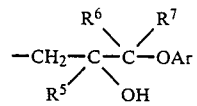

where R$^5$, R$^6$ and R$^7$ are each a hydrogen atom or a methyl group and at least one is a hydrogen atom; and Ar is a phenyl group (optionally substituted by one or two C$_{1-4}$ alkyl, C$_{1-4}$ alkoxy, C$_{1-4}$ alkylthio, C$_{1-4}$ alkylsulphinyl, C$_{1-4}$ alkylsulphonyl, halogen or trifluoromethyl groups); and the physiologically acceptable salts and complexes (eg cyclodextrin complexes) thereof.

The structural formulae herein are to be understood to include the enantiomers of each of the compounds concerned as well as mixtures of the enantiomers including racemates.

In general, the compounds of formula (1) in which the carbon atom carrying the group —(CH$_2$)$_n$X(CH$_2$)$_m$CO$_2$CH$_2$COR$^1$ and/or the carbon atom in the group Y carrying the —OH group are in the R-configuration (particularly the former) and mixtures containing such isomers are preferred.

When R$^1$ in the compounds of formula (1) is phenyl substituted by —CO$_2$H the compounds are capable of salt formation with bases. Examples of suitable salts are alkali metal (e.g. sodium and potassium), alkaline earth metal (e.g. calcium) and amine (e.g. piperazine) salts.

The term 'alkyl' as a group or part of a group within the definition of the compounds of formula (1) is intended to cover straight or branched chain moieties and may be, for example, a methyl ethyl, n-propyl, i-propyl, n-butyl, s-butyl or t-butyl group. The term 'halogen' means fluorine, chlorine, bromine or iodine.

A particular group of compounds of formula (1) are those wherein n, m, X and Y are as defined above and R$^1$ is phenyl optionally substituted by C$_{1-4}$ alkyl, C$_{1-4}$ alkoxy, C$_{1-4}$ alkanoyl, methylthio, methylsulphinyl, methylsulphonyl, halogen, —CO$_2$R$^2$ (where R$^2$ is a hydrogen atom or C$_{1-4}$ alkyl or phenyl), —CONR$^3$R$^4$ (where R$^3$ and R$^4$ may be the same or different and are each a hydrogen atom or a C$_{1-4}$ alkyl group), —NHCOR$^2$ (where R$^2$ is as defined just above) or —NHCONH$_2$.

In compounds where X is —CH=CH— or —CH$_2$—CH$_2$—, m is preferably 3 when n is 1, and m is preferably 2 or 4 when n is 2. When X is —CH=C=CH—, m is preferably 2 and n is 1, and 1 or 3 when n is 2.

When X is —CH=CH— it is preferably cis —CH=CH—.

The group R$^1$ is preferably a substituted phenyl group where the subsituent may be in the ortho, meta or, more particularly, para position, or is a 2-naphthyl group.

Compounds in which R$^1$ is a phenyl group substituted (particularly in the para position) by a methoxy, acetyl, —CO$_2$CH$_3$, —NHCOCH$_3$, benzoylamino, —CONH$_2$, —CON(CH$_3$)$_2$ or —CH$_2$CH(CONH$_2$)NHCOCH$_3$ group, or R$^1$ is a 2-naphthyl group are preferred.

Particularly preferred compounds are those in which R$^1$ is a para substituted phenyl group in which the substituent is —NHCOCH$_3$, benzoylamino, acetyl or —CONH$_2$.

In the group Y, R$^6$ and R$^7$ are preferably hydrogen atoms.

When the Ar phenyl group is substituted, the substituent may for example be methyl, ethyl, propyl, butyl, methoxy, ethoxy, propoxy, butoxy, methylthio, methylsulphinyl, methylsulphonyl, fluoro, chloro, bromo or trifluoromethyl. Preferably, only a single substituent is present, particularly at the para position. In general, Ar is preferably phenyl or phenyl substituted by halogen, particularly fluoro or chloro.

The preferences indicated above apply both separately and in combination with one or more of the other stated preferences.

A preferred group of compounds of the invention are compounds of formula (1) in which: X is —CH=CH— or —CH$_2$CH$_2$— and n is 1 and m is 3 or n is 2 and m is 2 or 4, or X is —CH=C=CH— and n is 1 and m is 2 or n is 2 and m is 1 or 3;

R$^1$ is a phenyl group substituted (preferably in the para-position) by —NHCOCH$_3$, benzoylamino, acetyl or —CONH$_2$:

R$^5$ is a hydrogen atom or a methyl group;

R$^6$ and R$^7$ are hydrogen atoms; and

Ar is phenyl or phenyl substituted by fluoro or chloro; and complexes (eg cyclodextrin complexes) thereof.

Compounds of this type in which the carbon atom carrying the —(CH$_2$)$_n$X(CH$_2$)$_m$CO$_2$CH$_2$COR$^1$ group is in the R- configuration are particularly preferred. Compounds of this type in which X is cis —CH=CH— and n is 1 and m is 3 or n is 2 and m is 2 or 4, especially where n is 1 and m is 3 or n is 2 and m is 2, are also particularly preferred.

Compounds of formula (1) inhibit gastric acid secretion, as determined for example by their ability to inhibit histamine-induced secretory responses in the rat perfused stomach, following the method of Ghosch and Schild in Br. J. Pharmacol., 1958, 13, 54 as modified by Parsons M. E., Ph.D Thesis, Univerisity of London, 1969.

The compounds also provide gastrointestinal cytoprotection, as determined for example by their ability to inhibit ethanol-induced lesions in the conscious rat, following the method of Robert et al in Gastroenterology, 1979, 77, 433, modified by the use of 5 mg/kg/s.c. indomethacin prior to the administration of the test compound.

Compounds of the invention are also able to lower lipid levels as may be demonstrated in standard animal models for example by determining their ability to lower non-esterified fatty acid levels in the starved rat (P. P. Lovisolo et. al., *Pharmacological Research Communications*, 1981, 13, 163–174; E. Schillinger and O. Loge, *Biochemical Pharmacology*, 1974, 23, 2283–2289).

The compounds are thus of interest in the prevention and/or treatment of ulcers. They may also be used in the treatment of other conditions which arise from the hypersecretion of gastric acid. The compounds may also be used for the prevention and/or treatment of conditions in which the underlying aetiology is associated with lipid imbalance or hyperlipidemia.

According to a further aspect of the present invention we therefore provide a compound of formula (1) or a physiologically acceptable salt or complex (e.g. cyclodextrin complex) thereof for use in the prevention and/or treatment of ulcers and other conditions arising from hypersecretion of gastric acid. We also provide a compound of formula (1) or a physiologically acceptable salt or complex (e.g. cylcodextrin complex) thereof for use in the prevention and/or treatment of conditions in which the underlying aetiology is associated with lipid imbalance or hyperlipidemia.

According to another aspect of the invention we provide a method of treating the human or non-human animal body to combat ulcers and other conditions arising from hypersecretion of gastric acid or conditions in which the underlying aetiology is associated with lipid imbalance or hyperlipidemia, which method comprises administering to the said body an effective amount of a compound of formula (1) or a physiologically acceptable salt or complex (e.g. cyclodextrin complex) thereof.

It will be appreciated that the compounds according to the invention may advantageously be used in conjunction with one or more other therapeutic agents, such as non-steroidal anti-inflammatory agents, or different anti-ulcer agents. It is to be understood that the present invention covers the use of a compound of formula (1) or a physiologically acceptable salt or complex (e.g. cyclodextrin complex) thereof in combination with one or more other therapeutic agents.

In a further aspect of the present invention we provide a pharmaceutical composition comprising as an active ingredient a compound of formula (1) or a physiologically acceptable salt or complex (e.g. cyclodextrin complex) thereof together with one or more pharmaceutical carriers or excipients.

Compounds may be formulated in conventional manner with one or more pharmaceutical carriers, for example for oral, buccal, parenteral or rectal administration.

The compounds may be formulated for oral administration as, for example, powders, solutions or syrups prepared by conventional means with acceptable excipients.

The compounds may be formulated for parenteral administration by bolus injections or continuous infusion. Formulations for injections may be presented in unit dosage form in ampoules, or in multi-dose containers, with an added preservative.

For buccal administration, the compounds may be formulated as tablets or lozenges in conventional manner; and for rectal administration compositions such as suppositories or retention enemas, for example containing conventional suppository bases such as cocoa butter or other glyceride, can be used.

The compounds are preferably administered orally, for example in amounts of 0.5 to 300 μg/kg body weight, 1 to 4 times daily. For parenteral administration, the compounds may be administered in amounts of 0.01 to 10 μg/kg body weight, 1 to 4 times daily. The precise dose will of course depend on the age and condition of the patient.

Suitable methods for preparing the compounds of the invention are described below, the various groups and symbols being as defined above except where otherwise indicated.

(a) Compounds of formula (1) may be prepared by deprotection of a compound of formula (2)

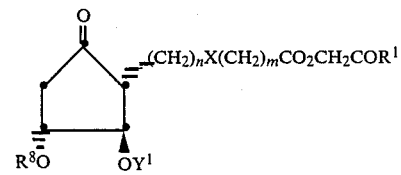
(2)

in which Y$^1$ is defined as a group

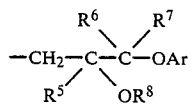

and $R^8$ is a suitable hydroxyl protecting group (e.g. tetrahydropyran-2-yl, tetrahydrofuran-2-yl, ethoxyethyl, tri(hydrocarbyl)silyl or arylmethyl.

The two $R^8$ groups in the compounds of formula (2) are conveniently the same, but they may be different if desired.

Where $R^8$ is tri(hydrocarbyl)silyl the hydrocarbyl substituents may be the same or different e.g. $C_{1-6}$ alkyl, $C_{2-6}$ alkenyl, $C_{3-7}$ cycloalkyl, $C_{7-20}$ aralkyl and $C_{6-20}$ aryl groups. Such groups include methyl, ethyl, n-propyl, isopropyl, n-butyl, isobutyl, t-butyl, allyl, phenyl and benzyl. Preferred hydrocarbyl groups are $C_{1-4}$ alkyl, e.g. methyl and t-butyl. Trimethylsilyl and t-butyldimethylsilyl groups are particular preferred.

When $R^8$ is an arylmethyl group it may contain up to 20 carbon atoms, e.g. benzyl, diphenylmethyl or triphenylmethyl.

The method used to deprotect the protected hydroxyl group will depend on the nature of $R^8$ but in general acid hydrolysis or reduction may be used.

Thus, for example when $R^8$ is a tetrahydropyran-2-yl, tetrahydrofuran-2-yl or ethoxyethyl group deprotection may be carried out with an acid. Suitable acids include inorganic acids such as hydrochloric acid and organic acids such as acetic acid or trifluoroacetic acid. Suitable solvents include ethers (e.g. diethyl ether, dioxan and tetrahydrofuran), halogenated hydrocarbons (e.g. dichloromethane), hydrocarbons (e.g. toluene), dipolar aprotic solvents (e.g. acetone, acetonitrile, dimethylsulphoxide and dimethylformamide) and alcohols (e.g. methanol, ethanol and ethylene gylcol). Where desired the solvents may be used in combination with water. The reaction may be carried out at any suitable temperature, such as from 0° to 50° C., e.g. 40° to 50° C.

A tri(hydrocarbyl)silyl group may for example be removed by acid hydrolysis, e.g. with dilute mineral acid or trifluoroacetic acid or by treatment with fluoride ion (e.g. from a quaternary ammonium fluoride such as tetra-n-butyl ammonium fluoride), or by treatment with aqueous hydrogen fluoride. Arylmethyl groups may be removed by reduction, e.g. by hydrogenolysis, e.g. with a noble metal catalyst such as platinum or palladium, or by treatment with a Lewis acid (e.g. boron trifluoride-etherate) in the presence of a thiol (e.g. ethanethiol) in a suitable solvent such as dichloromethane at e.g. room temperature.

Compounds of formula (2) may be prepared by oxidation of a compound of formula (3)

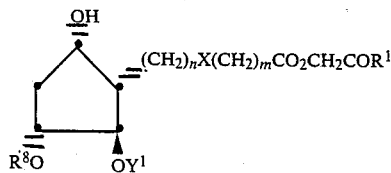 (3)

(where $R^8$ and $Y^1$ are as defined above) with, for example, pyridinium chlorochromate in the presence of a buffer (e.g. sodium acetate) in a suitable solvent (e.g. dichloromethane) at an appropriate temperature (e.g. room temperature). Alternatively, the oxidation may be carried out with dimethylsulphoxide, activated by N,N'-dicyclohexylcarbodiimide, in the presence of pyridinium trifluoroacetate in a solvent such as dichloromethane at e.g. room temperature. Other conventional oxidative methods can also be used, for example Jones reagent.

It will be appreciated that the deprotection method (a) is usually applied in connection with the formation by oxidation of the cyclopentyl ring oxo group. Thus the compounds of formula (1) may generally be prepared by oxidising a corresponding compound of formula (3) and removing the protecting groups thereafter. The formation of the ring oxo group may also however be effected prior to the introduction of the desired ester group by alkylation (e.g. by method (b) below) and the two protecting groups removed thereafter.

Compounds of formula (3) may be prepared by alkylation of the corresponding carboxylic acids using the method described in process (b) below.

(b) Compounds of formula (1) may also be prepared by alkylation of the corresponding carboxylic acid of formula (4)

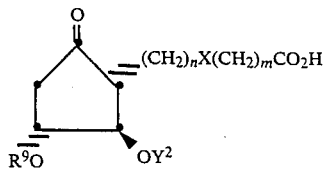 (4)

(where $R^9$ is a hydrogen atom or a group $R^8$ as defined above and $Y^2$ is a group Y or $Y^1$ as defined above) with a ketone of formula (5)

$$ZCH_2COR^1 \qquad (5)$$

in which Z is a leaving group such as halogen (e.g. bromine) followed, if necessary, by removal of any protecting groups present. The alkylation reaction is preferably carried out in the presence of a base such as diisopropylethylamine or potassium fluoride in a solvent such as acetonitrile or dimethylformamide at a suitable temperature (e.g. room temperature). The deprotection may be effected according to the methods described in process (a) above.

The carboxylic acids required as starting materials for the reactions described in processes (a) and (b) may be prepared by the methods generally described in European Patent Specification No. 160495.

Ketones of formula (5) are known compounds or may be prepared by methods analogous to those used for the preparation of the known compounds.

(c) Compounds of formula (1) in which X is a —CH<sub>2</sub>—CH<sub>2</sub>— group may be prepared by reduction of a corresponding compound in which X is a cis or trans —CH=CH— group or an acetylene group. Suitable methods of reduction include hydrogen in the presence of a catalyst, e.g. palladium, on a support (e.g. carbon). Suitable solvents include ethyl acetate, ethanol and methanol.

(d) Compounds of formula (1) in which X is a —CH=CH— group may be prepared by selective reduction of a corresponding compound in which X is an acetylene group. Suitable methods of reduction include hydrogen in the presence of a catalyst, e.g. palladium on a support (e.g. $CaCO_3$ or $BaSO_4$) and poisoned for example by lead or quinoline. Suitable solvents include ethyl acetate and methanol. This reaction is particularly suitable for the preparation of compounds in which X is cis —CH=CH—.

The acetylenes required as starting materials may be prepared by the methods generally described in European Patent Specification No. 160495.

(e) Compounds of formula (1) in which X is a trans —CH=CH— group may be prepared by isomerisation of a corresponding compound in which X is a cis —CH=CH— group. The isomerisation may, for example, be effected by treating the corresponding cis compound with toluene-p-sulphinic acid in dioxan (e.g. at reflux), azobisisobutyronitrile and thiophenol, using for example a hydrocarbon solvent (e.g. benzene) at any suitable temperature up to reflux.

(f) Where salts of compounds of formula (1) are desired such salts may be formed by conventional methods e.g. by treating an acid of formula (1) with a base (e.g. an amine such as piperazine) in a solvent such as ether.

Complexes (e.g. cyclodextrin complexes) may be prepared using conventional methods e.g. by treating a compound of formula (1) with $\alpha$-, $\beta$- or $\gamma$-cyclodextrin in a suitable solvent.

The processes in methods (b)–(f) may also be applied to compounds of formula (2) and in particular formula (3) and the products subsequently converted into compounds of formula (1) by the methods described above.

When a specific enantiomer of formula (1) is required, starting materials having the desired stereochemical configuration should be used in the above processes. Such starting materials may be prepared for example using the methods described in European Patent Specification No. 160495 from an enantiomeric intermediate as described in European Patent Specification No. 74856.

The following examples illustrate the invention. Temperatures are in °C.
'Dried' refers to drying with anhydrous MgSO$_4$.
T.l.c.—Thin layer chromatography on silica.
Chromatography was carried out on silica gel.
The following abbreviations are used: ER—ether; EA—ethyl acetate; PE—petroleum ether (b.p. 40°-60° unless otherwise stated); THF—tetrahydrofuran; CH$_2$Cl$_2$—dichloromethane; CHBr$_3$—bromoform; MeOH—methanol; DMF—dimethylformamide; CHCl$_3$—chloroform.

INTERMEDIATE 1

(1a) N-[4-(Bromoacetyl)phenyl]acetamide (1b) 4-(Bromoacetyl)benzamide (1c) N-[4-(Bromoacetyl)phenyl]benzamide The above intermediates were prepared by the literature procedures described in *J. Prakt. Chem.*, 1969, 311, 168.

INTERMEDIATE 2

(2a) [1S-[1$\alpha$(Z), 2$\beta$(2S*), 3$\alpha$, 5$\alpha$]]-7-[5-Hydroxy-2-[3-phenoxy-2-[(tetrahydro-2H-pyran-2-yl)oxy]propoxy]-3-[(tetrahydro-2H-pyran-2-yl)oxy]cyclopentyl]-5-heptenoic acid Prepared as described in European Patent Specification No. 160495.

(2b) [1S-[1$\alpha$(Z), 2$\beta$(2S*), 3$\alpha$, 5$\alpha$]]-7-[5-Hydroxy-2-[3-phenoxy-2-[(tetrahydro-2H-pyran-2-yl)oxy]propoxy]-3-[(tetrahydro-2H-pyran-2-yl)oxy]cyclopentyl]-4-heptenoic acid Prepared as described in GB-A-2174702

INTERMEDIATE 3

(3a) [1S-[1$\alpha$(Z), 2$\beta$(2S*), 3$\alpha$, 5$\alpha$]]-(+)-2-[4-(Acetylamino)phenyl]-2-oxethyl 7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-5-heptenoate A solution of Intermediate 1a (0.28 g) and potassium fluoride (0.16 g) in dry DMF (5 ml) was stirred at 23° for 15 min. A solution of Intermediate 2a (0.7 g) in dry DMF (3 ml) was added and the mixture stirred at 23° for 1.0 h. The mixture was diluted with ER (30 ml) and washed consecutively with water (5×25 ml), brine (25 ml), dried and evaporated to give the title compound as a white foam (0.75 g). I.r. (CHBr$_3$) 3420, 1740, 1700 cm$^{-1}$. [$\alpha$] $_D^{20}$+18° (CHCl$_3$).

The following compound was prepared in a similar manner:

(3b) [1S-[1$\alpha$(Z), 2$\beta$(2S*), 3$\alpha$, 5$\alpha$]]-2-[4-(Aminocarbonyl)phenyl]-2-oxoethyl 7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-5-heptenoate I.r. (CHBr$_3$) 3580, 3520, 3400, 1730, 1710, 1680 cm$^{-1}$.
From Intermediates 1b and 2a.

INTERMEDIATE 4

(4a)
[1S-[1$\alpha$(Z),2$\beta$(2S*),3$\alpha$,5$\alpha$]]-2-[4-(Benzoylamino)-phenyl]-2-oxoethyl 7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-4-heptenoate A solution of Intermediate 1c (0.27 g) and potassium fluoride (0.13 g) in dry DMF (10 ml) was stirred at room temperature for 30 min. A solution of Intermediate 2b (0.43 g) in DMF (3 ml) was then added. The solution was stirred at room temperature for 4 h, water (50 ml) added and the solution extracted with ether (3×50 ml), dried and the solvent removed in vacuo. The residue was purified by flash chromatography (Merck 9385) eluting with EA-PE (3:1) to yield the title compound as a colourless oil (0.66 g). T.l.c. (1:1, EA-PE) Rf 0.14.

The following compound was prepared in a similar manner:

(4b)
[1S-[1$\alpha$(Z),2$\beta$(2S*),3$\alpha$,5$\alpha$]]-2-[4-(Aminocarbonyl)-phenyl]-2-oxoethyl-7-[5-hydroxy-2-[3-phenoxy-2-[(tetrahydro-2H-pyran-2-yl)oxy]propoxy]-3-[(tetrahydro-2H-pyran-2-yl)oxy]cyclopentyl-4-heptenoate (0.52 g) as a pale yellow oil. T.l.c. (EA) Rf 0.28.
From Intermediate 1b (0.14 g) and Intermediate 2b (0.31 g) except that the purification step was not necessary.

INTERMEDIATE 5

[1S-[1α(Z),2β(2S*),3α,5α]]-2-[4-Acetylamino)phenyl]-2-oxoethyl 7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-4-heptenoate Potassium fluoride (94 mg) and Intermediate 1a (150 mg) were added to a solution of Intermediate 2b (300 mg) in dry DMF (4 ml) at 20°. After 6h the mixture was diluted with EA (30 ml) and washed consecutively with water (2×20 ml), 8% sodium bicarbonate (2×20 ml) and brine (20 ml). The organic extract was dried, filtered and evaporated to yield the title compound (429 mg) as a yellow oil. T.l.c (EA) Rf 0.33.

INTERMEDIATE 6

(6a) [1R-[1α(Z), 2β(2R*), 3α]]-(−)-2-[4-(Acetylamino)phenyl]-2-oxoethyl 7-[5-oxo-2-[3-phenoxy-2-[(tetrahydro-2H-pyran-2-yl)oxy]propoxy]-3-[(tetrahydro-2H-pyran-2-yl)oxy]cyclopentyl]-5-heptenoate Pyridinium chlorochromate (0.60 g) was added to a stirred solution of Intermediate 3a (0.7 g) and anhydrous sodium acetate (0.46 g) in dry $CH_2Cl_2$ (25 ml) at 0°. The mixture was stirred at 0° for 1h, at 0°–23° over 2h, was diluted with EA (30 ml) and filtered through a small wad of acid-washed silica (pH 3.8). The filtrate was evaporated in vacuo below 40° and the residue purified by chromatography on acid washed silica (pH 3.8) eluting with EA-cyclohexane (4:1) to give the title compound as an oil (0.425 g). I.r. ($CHBr_3$) 3470, 1735, 1700, 1515 cm$^{-1}$. $[\alpha]_D^{20}$ −11.6° ($CHCl_3$).

The following compound was prepared in a similar manner:

(6b) [1R-[1α(Z), 2β(2R*), 3α]]-2-[4-(Aminocarbonyl)phenyl]-2-oxoethyl 7-[5-oxo-2-[3-phenoxy-2-[(tetrahydro-2H-pyran-2-yl)oxy]propoxy]-3-[(tetrahydro-2H-pyran-2-yl)oxy]cyclopentyl]-5-heptenoate T.l.c. (EA) Rf 0.64.
From Intermediate 3b.

INTERMEDIATE 7

[1R-[1α(Z),2β(2R*),3α]]-2-[4-Acetylamino)phenyl]-2-oxoethyl 7-[5-oxo-2-[3-phenoxy-2-[(tetrahydro-2H-pyran-2-yl)oxy]propoxy]-3-[(tetrahydro-2H-pyran-2-yl)oxy]cyclopentyl]-4-heptenoate Pyridinium chlorochromate (361 mg), sodium acetate (274 mg) and ground 3A molecular sieves (400 mg) were added to an ice-cold solution of Intermediate 5 (412 mg) in dry $CH_2Cl_2$ (10 ml) at 0°–5°. After 3.5h the mixture was diluted with EA (30 ml) and filtered through a silica pad (Merck 9385). The filtrate was washed with water (30 ml) and the organic extract dried, filtered and evaporated to leave an oily residue. The residue was purified by flash chromatography (Merck 9385, acid washed to pH 3.8) eluting with EA-hexane (2:1) to give the title compound (230 mg) as a yellow gum. T.l.c. (2:1, EA-hexane) Rf 0.28.

INTERMEDIATE 8

(8a) [1R-[1α(Z),2β(2R*),3α]]-2-[4-(Benzoylamino)phenyl]-2-oxoethyl-7-[5-oxo-2-[3-phenoxy-2-[(tetrahydro-2H-pyran-2-yl)oxy]propoxy]-3-[(tetrahydro-2H-pyran-2-yl)oxy]cyclopentyl]-4-heptenoate Pyridinium chlorochromate (0.54 g) was added to a solution of Intermediate 4a in dry $CH_2Cl_2$ (20 ml) containing anhydrous sodium acetate (0.54 g) and powdered 3Å molecular sieves (0.5 g) at 0°. The solution was allowed to warm to room temperature for 2h, EA (50 ml) added and the suspension filtered through hyflo. The solvent was removed in vacuo and the residue purified by flash chromatography (Merck 9385, acid-washed to pH 4) eluting with EA-PE (1:1) to yield the title compound as a pale yellow oil (0.52 g). T.l.c. (1:1, EA-PE) Rf 0.25.

The following compound was prepared in a similar manner:

(8b) [1R-[1α(Z),2β(2R*),3α]]-2-[4-(Aminocarbonyl)-phenyl]-2-oxoethyl 7-[5-oxo-2-[3-phenoxy-2-[(tetrahydro-2H-pyran-2-yl)oxy]propoxy]-3-[(tetrahydro-2H-pyran-2-yl)oxy]cyclopentyl]-4-heptenoate (0.265 g) as a colourless oil. T.l.c. (EA) Rf 0.45.

From Intermediate 4b (0.48 g) except that flash chromatograhy was effected using EA as the eluant.

EXAMPLE 1

[1R-[1α(Z), 2β(R*), 3α]]-(−)-2-[4-(Acetylamino)phenyl]-2-oxoethyl 7-[3-hydroxy-2-(2-hydroxy-3-phenoxypropoxy)-5-oxocyclopentyl]-5-heptenoate A solution of Intermediate 6a (0.39 g) in acetic acid-water-THF (20:10:3, 15 ml) was stirred at 40° for 4.5h. The mixture was evaporated in vacuo below 45° and the residue was twice diluted with toluene (35 ml) and re-evaporated in vacuo. The residual white solid was slurried in ER (20 ml) and then crystallised from EA-cyclohexane to give the title compound as a white solid (0.16 g), m.p. 114°–6°. $[\alpha]_D^{20}$ −20.1° ($CHCl_3$).

Analysis Found: C,65.4; H,6.6; N,2.4. $C_{31}H_{37}NO_9$ requires C,65.6; H,6.6; N,2.5%.

EXAMPLE 2

[1R-[1α(Z), 2β(R*), 3α]]-2-[4-(Aminocarbonyl)phenyl]-2-oxoethyl 7-[3-hydroxy-2-(2-hydroxy-3-phenoxypropoxy)-5-oxocyclopentyl]-5-heptenoate A solution of Intermediate 6b (0.38 g) in acetic aicd-water-THF (20:10:3, 5 ml) was stirred at 40° for 3.5h. The mixture was evaporated in vacuo and the residue was diluted with toluene (25 ml) and evaporated. Purification by chromatography on acid-washed silica gel (pH 3.8) using EA increasing to 9:1 EA-MeOH as eluant afforded, after trituration with ER, the title compound as a white solid (0.56 g), m.p. 64°–66°. T.l.c. (9:1, EA-MeOH) Rf 0.33.

EXAMPLE 3

(3a)

[1R-[1α(Z),2β(2R*),3α]]-2-[4-Acetylamino)phenyl]-2-oxoethyl 7-[3-hydroxy-2-(2-hydroxy-3-phenoxypropoxy)-5-oxocyclopentyl]-4-heptenoate A solution of Intermediate 7 (210 mg) in acetic acid-water-THF (6:3:1; 7 ml) was stirred at 40° for 4.5h. The mixture was concentrated in vacuo to leave an oily residue which was purified by flash chromatography (Merck 9385, acid washed to pH 3.8) eluting with EA to give the title compound (85 mg) as an opaque gum. T.l.c. (EA) Rf 0.23.

Analysis Found: C,65.32; H,6.88; N,2.32. $C_{31}H_{37}NO_9$ requires C,65.59; H,6.57; N,2.47%.

The following compound was prepared in a similar manner:

(3b)

[1R-[1α(Z),2β(R*),3α]]-2-[4-(Aminocarbonyl)phenyl]-2-oxoethyl 7-[3-hydroxy-2-(2-hydroxy-3-phenoxypropoxy)-5-oxocyclopentyl]-4-heptenoate (108 mg) as a white foam, m.p. 82°-88°. T.l.c. (1:9, MeOH-ER) Rf 0.25.

Analysis Found: C,64.44; H,5.39; N,2.70. $C_{30}H_{35}NO_9$ requires C,65.09; H,6.37; N,2.53%.

From Intermediate 8b (0.26 g) except that flash chromatography was effected using MeOH-ER (1:9) as eluant.

EXAMPLE 4

[1R-[1α(Z),2β(R*),3α]]-2-[4-(Benzoylamino)phenyl]-2-oxoethyl-7-[3-hydroxy-2-(2-hydroxy-3-phenoxypropoxy)-5-oxocyclopentyl]-4-heptenoate A solution of Intermediate 8a (0.52 g) in acetic acid-water-THF (6:3:1, 10 ml) was stirred at 40° for 4h. The solution was concentrated in vacuo and the residue purified by flash chromatography (Merck 9385, acid washed to pH 3.8) eluting with 1:1 EA-PE→EA to give the title compound (0.205 g) as a white solid, m.p. 82°-86°. T.l.c. (EA) Rf 0.44.

Analysis Found: C,68.29; H,5.96; N,2.06. $C_{36}H_{39}NO_9$ requires C,68.67; H,6.24; N,2.22%.

The following are examples of pharmaceutical formulations using compounds of the invention. In the examples, the term "active ingredient" is used to denote a compound of the invention, such as a compound described in the preceding examples.

1. Tablets

These may be prepared by direct compression

|  | mg/tablet |
| --- | --- |
| Active Ingredient | 0.015 to 0.2 |
| Magnesium stearate, BP | 1.5 |
| Microcrystalline cellulose, USP to compression weight | 150.0 |

The active ingredient is blended with about 10% of the microcrystalline cellulose then blended with the remaining microcrystalline cellulose and magnesium stearate. The blend is then compressed using 6 mm diameter punches into tables on a suitable machine.

The tablets may be film coated with suitable film forming materials e.g. methyl cellulose of hydroxypropyl methylcellulose using standard techniques.

2. Capsules

|  | mg/tablet |
| --- | --- |
| Active ingredient | 0.015 to 0.2 |
| Magnesium stearate, BP | 1.0 |
| *Starch 1500 to fill weight | 100.0 |

*A form of directly compressible starch.

The active ingredient is preblended with some of the Starch 1500 then this preblend is mixed with the remaining Starch 1500 and magnesium stearate. The mix is then filled into size No 2 hard gelatin capsule shells using suitable machinery.

We claim:

1. Compounds of the general formula (1)

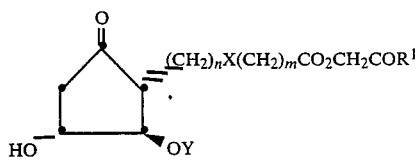

wherein n is 1 or 2;

m is 2-5 and X is cis of trans —CH═CH— or —CH$_2$—CH$_2$—; or m is 1-4 and X is —CH═C═CH—;

$R^1$ is phenyl, substituted phenyl, wherein said substituent is $C_{1-4}$ alkyl, $C_{1-4}$ alkoxy, $C_{1-4}$, alkanoyl, methylthio, methylsulphinyl, methylsulphonyl, halogen, —CO$_2$R$^2$ (wherein $R^2$ is a hydrogen atom or $C_{1-4}$ alkyl or phenyl), —CONR$^3$R$^4$ (where $R^3$ and $R^4$ may be the same or different and are each of hydrogen atom or a $C_{1-4}$ alkyl group), —NHCOR$^2$ (where $R^2$ is a hydrogen atom, $C_{1-4}$ alkyl, phenyl, and phenyl substituted by a hydroxyl, CH$_3$CONH— or benzoylamino), —NHCONH$_2$, —CH$_2$CH(CONH$_2$)NHCOCH$_3$,

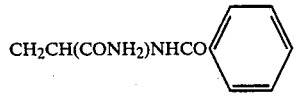

or $R^1$ is 2-naphthyl;

Y is

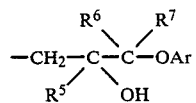

wherein $R^5$, $R^6$ and $R^7$ are each a hydrogen atom or a methyl group and at least one is a hydrogen atom; and Ar is a phenyl group, or a phenyl group substituted by one or two $C_{1-4}$ alkyl, $C_{1-4}$ alkoxy, $C_{1-4}$ alkylthio, $C_{1-4}$ alkylsulphinyl, $C_{1-4}$ alkylsulphonyl, halogen, or trifluoromethyl groups; and the physiological acceptable salts and complexes thereof.

2. Compounds as claimed in claim 1 in which X is —CH═CH— or —CH$_2$—CH$_2$— and m is 3 when n is 1 and m is 2 or 4 when n is 2; or X is —CH=C=CH— and m is 2 when n is 1 and m is 1 or 3 when n is 2.

3. Compounds as claimed in claim 1 in which $R^1$ is phenyl substituted by a methoxy, acetyl, —CO$_2$CH$_3$, —NHCOCH$_3$, benzoylamino, —CONH$_2$, —CON(CH$_3$)$_2$ or —CH$_2$CH(CONH$_2$)NHCOCH$_3$ group, or $R^1$ is a 2-naphthyl group.

4. Compounds as claimed in claim 1 in which $R^6$ and $R^7$ are hydrogen atoms and Ar is phenyl or phenyl substituted by fluoro or chloro.

5. Compounds as claimed in claim 1 in which:

X is —CH=CH— or —CH$_2$—CH$_2$— and n is 1 and m is 3 or n is 2 and m is 2 or 4, or X is —CH=C=CH— and n is 1 and m is 2 or n is 2 and m is 1 or 3;

$R^1$ is a phenyl group substituted by —NHCOCH$_3$, benzoylamino, acetyl or —CONH$_2$ $R^5$ is a hydrogen atom or a methyl group;

$R^6$ and $R^7$ are hydrogen atoms; and

Ar is phenyl or phenyl substituted by fluoro or chloro; and complexes thereof.

6. Compounds as claimed in claim 5 in which X is cis —CH=CH—.

7. Compounds as claimed in claim 5 in which X is cis —CH=CH—, and n is 1 and m is 3 or n is 2 and m is 2.

8. Compounds as claimed in claim 1 in which the carbon atom carrying the group —(CH$_2$)$_n$X(CH$_2$)$_m$CO$_2$CH$_2$COR$^1$ is in the R-configuration.

9. Compunds as claimed in claim 1 in which R' is a phenyl group containing a single substituent in the para position.

10. A pharmaceutical composition, comprising a compound as claimed in claim 1 together with one or more pharmaceutical carriers.

11. A process for the preparation of a compound as claimed in claim 1 which comprises:

(a) deprotecting a compound of the general formula (2)

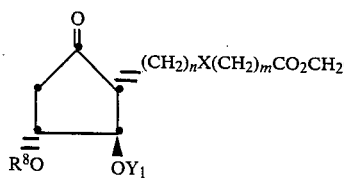

(2)

wherein
n is 1 or 2;
m is 2-5 and X is cis or trans —CH=CH— or —CH$_2$—CH$_2$—; or m is 1-4 and X is —CH=C=CH—;
$R^1$ is a phenyl, phenyl substituted with a substituent selected from C$_{1-4}$ alkyl, C$_{1-4}$ alkoxy, C$_{1-4}$ alkanoyl, methylthio, methylsulphinyl, methylsulphonyl, halogen, —CO$_2$R$^2$ (where R$^2$ is selected from a hydrogen atom, C$_{1-4}$ alkyl or phenyl) —CONR$^3$R$^4$ (where R$^3$ and R$^4$ may be the same or different and are each a hydrogen atom or a C$_{1-4}$ alkyl group), —NHCOR$^2$ (where R$^2$ is selected from a hydrogen atom, C$_{1-4}$ alkyl, phenyl, a phenyl group substituted by hydroxyl, CH$_3$CONH— or benzoylamino), —NHCONH$_2$, —CH$_2$CH(CONH$_2$)NHCOCH$_3$,

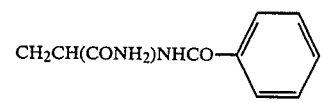

or $R^1$ is 2-naphthyl;
$Y^1$ is

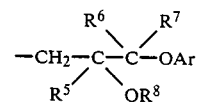

where $R^5$, $R^6$, and $R^7$ are each a hydrogen atom or a methyl group and at least one is a hydrogen atom;
Ar is phenyl group or a phenyl group substituted by one or two C$_{1-4}$ alkyl, C$_{1-4}$ alkoxy, C$_{1-4}$ alkylthio, C$_{1-4}$ alkylsulphinyl, C$_{1-4}$ alkylsulphonyl, halogen or trifluoromethyl groups; and
$R^8$ is a hydroxyl protecting group;

(b) alkylating the corresponding carboxylic acid of formula (4)

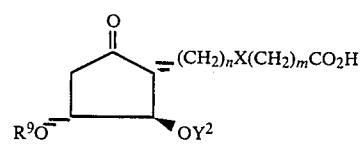

(4)

(where $R^9$ is a hydrogen atom or a hydroxyl protecting group and $Y^2$ is a group Y or such a group in which the hydroxyl group is protected) with a ketone of formula (5)

 (5)

in which Z is a leaving group, followed if necessary by removal of any protecting groups present;

(c) in the preparation of a compound in which X is